United States Patent [19]
Adamoli, Jr. et al.

[11] Patent Number: 5,951,995
[45] Date of Patent: Sep. 14, 1999

[54] USES FOR CELLULOSE-CONTAINING AGGREGATES

[76] Inventors: James R. Adamoli, Jr., 1326 Country Place Cir., Houston, Tex. 77079; Mark A. Adamoli, 14316 Misty Meadow, Houston, Tex. 77079

[21] Appl. No.: 08/880,901

[22] Filed: Jun. 23, 1997

Related U.S. Application Data

[63] Continuation-in-part of application No. 08/479,171, Jun. 7, 1995, abandoned, which is a continuation-in-part of application No. 08/228,443, Apr. 15, 1994, abandoned.

[51] Int. Cl.$^6$ .................................................. A01N 25/10
[52] U.S. Cl. ...................... 424/408; 424/76.6; 424/406; 424/413
[58] Field of Search .................... 424/76.6, 413, 424/406

[56] References Cited

U.S. PATENT DOCUMENTS

| | | | |
|---|---|---|---|
| 3,645,893 | 2/1972 | Rohrer | 424/76.6 |
| 3,980,050 | 9/1976 | Neubauer | 119/1 |
| 4,311,115 | 1/1982 | Litzinger | 119/1 |
| 5,019,564 | 5/1991 | Low et al. | 514/75 |
| 5,082,563 | 1/1992 | Webb et al. | 210/631 |
| 5,195,465 | 3/1993 | Webb et al. | 119/172 |
| 5,352,780 | 10/1994 | Webb et al. | 536/56 |
| 5,429,741 | 7/1995 | Webb et al. | 210/663 |
| 5,486,068 | 1/1996 | Wilson | 405/129 |
| 5,622,697 | 4/1997 | Moore, Jr. | 424/76.6 |
| 5,674,806 | 10/1997 | Adamoli et al. | 504/116 |

OTHER PUBLICATIONS

Report—Waste Management Research, Extension, and Technology Transfer Activites by J. H. Edwards, National Soil Dynamics Laboratory, Auburn, AL Dec. 1994.
Termited–Ferrar Oecologia (Berl) 52 (1) pp. 139–146, 1982.
Steller et al Penn. Ag Expt. Sta. Summer/Fall vol. 15 #2 pp. 47–48—Termite feeding, 1982.
Morrison–Feeds & Feeding pp. 639–649 1954 Manurial Value of Feeding Stuffs.

*Primary Examiner*—Neil S. Levy
*Attorney, Agent, or Firm*—John R Casperson

[57] ABSTRACT

Aggregates containing cellulosic material can be used to remediate land which has been polluted by agricultural wastes and to prevent such pollution, as well as for carriers of insecticides and herbicides.

6 Claims, No Drawings

USES FOR CELLULOSE-CONTAINING AGGREGATES

This application is a continuation-in-part of copending application Ser. No. 08/479,171, now abd. filed Jun. 7, 1995, now pending, which was a continuation-in-part of then co-pending application Ser. No. 08/228,443, filed Apr. 15, 1994, now abandoned.

BACKGROUND OF THE INVENTION

This invention relates to the use of cellulose products such as recycled paper.

Certain cellulosic material, such as ground newsprint and other paper as well as agricultural and food byproducts, such as gin trash, hulls and peels, are difficult to handle and apply in large quantities. It has a low bulk density and paper products are subject to caking when exposed to moisture. A technique for making cellulosic material easier to handle and apply such as to agricultural lands would be desirable.

When applied to the surface of the soil, many cellulosic materials, such as ground paper, are easily blown by the wind. A technique to improve reliable placement of the cellulosic material for surface applications would be very desirable.

When buried in agricultural lands, ground newsprint is very resistant to degradation. A technique to improve the speed of degradation of buried ground newsprint would be desirable.

A major challenge facing producers of poultry, cattle, swine, horses and sheep is the disposal of the large amounts of animal waste generated. Poultry litter, especially, has a high nitrogen content. However, as a nutrient source for corn, poultry litter has proven to be a less effective source of nitrogen than commercial ammonium nitrate. This has sometime lead to excessive applications of poultry litter to farmland, resulting in contaminated runoffs. A technique for an environmentally sound soil treatment that utilizes animal waste has the potential for broad based benefits. A process for remediating contaminated areas would also be very desirable.

Waste products such as waste paper, lawn clippings, wood chips, gin trash, banana peels, shrubbery, sugar cane, sorghum, other vegetation and plastics are filling landfills. Alternatives to current disposal of these products would be very desirable.

Certain insects, such as termites and fire ants, are difficult to control and cause much damage. Improved techniques for controlling these insects would be very desirable.

Herbicides are used throughout the country to control the growth of unwanted plants. More effective techniques for applying herbicides would reduce the amount of herbicide being release into the environment and would be very desirable.

OBJECTS OF THE INVENTION

It is an object of this invention to provide cellulose-containing products, especially products formed from waste paper such as newsprint, in a form so that it is highly suitable for horticultural and agricultural uses, and for insect control.

It is a further object of this invention to provide a technique for using animal waste for horticultural and agricultural purposes.

It is another object of this invention to provide a technique for remediating land which has become polluted with animal wastes with by the use of cellulose-containing products, especially waste paper products.

It is a further object of this invention to provide a soil amendment technique using cellulosic material products, especially waste products such as waste paper, lawn clippings, wood chips, gin trash, banana peels, shrubbery, sugar cane, sorghum and other vegetation.

SUMMARY OF THE INVENTION

On embodiment of the invention is directed toward the treatment or remediation of land which has become or is at risk of becoming polluted by the application of animal wastes. The treatment in accordance with this embodiment of the invention is to apply aggregates of cellulose-containing particles to the land in a quantity sufficient to counteract the deleterious effects caused by the excess wastes.

In another embodiment of the invention, is provided a method for controlling termite infestation employing the aggregates as described above. In accordance with the method, an area to be protected from the termite infestation is selected and aggregates of cellulose-containing particles containing at least one anti-termite agent are applied around the area to be protected.

In another embodiment of the invention, the aggregates of cellulose particles as described above can be employed in a method for controlling fire ants. The method is carried out by selecting an area in which fire ant control is desired and applying aggregates of cellulose-containing particles containing a fire ant toxin to the area.

In another embodiment of the invention, the aggregates of cellulose particles as described above can be employed in a method for controlling plant growth. The method is carried out by selecting an area in which plant growth control is desired and applying aggregates of cellulose-containing particles containing a plant growth inhibitor to the area. Generally, the type of plant growth desired to be inhibited will be weed growth or grass growth. The area to be treated will generally comprise a horticultural area. In such case, the plant growth inhibitor will generally comprise an herbicide.

DETAILED DESCRIPTION OF THE PREFERRED EMBODIMENTS

Due to economics, a recent trend in the poultry, swine, dairy and cattle industries is for large numbers of animals to be confined at one location. Many of these agricultural operations use lagoons for waste treatment or directly land-apply the manure. Typically, the lagoon effluent is land applied for further treatment and ultimate disposal. However, it is generally not economically feasible to transport the lagoon effluent or manure off-site or to purchase large tracts of land for disposal. Therefore, excess levels of plant nutrients build up in soils when effluent from water treatment lagoons and manure is repeatedly applied to small parcels of land adjacent to large animal feeding operations. The high levels of nitrogen and phosphorus that are often found in the soil at land application sites have the potential to degrade surface water and ground water supplies. The U.S. Environmental Protection Agency has set a maximum contaminate level (MCL) at 10 mg/L NO3—N in drinking water.

On embodiment of the invention is directed toward the treatment or remediation of land which has become polluted by the application of animal wastes.

The treatment in accordance with this embodiment of the invention is to apply aggregates of cellulose-containing particles to the land in a quantity sufficient to counteract the deleterious effects caused by the excess wastes.

The cellulose containing particles are generally of paper and/or vegetable matter origin. When paper is present in the aggregates, it can be present over a wide range. For example, the paper can be present in an amount to provide the aggregate with a paper content in the range of from about 1% to about 99% by weight. Any paper can be used, but the invention will probably have its greatest benefit when applied to recycled paper, including newspapers, telephone books, magazines, computer paper, corrugated paper, etc. Waste or excess paper or pulp recovered from manufacturing processes can also be used. The selection of the desired paper is an economic one, rather than a technical one. Vegetable matter which can be employed as cellulose-containing particles includes include wastes from the timber and wood products industry, such as wood, wood chips, lumber, and sawdust, wastes from landscaping work such as brush, branches, grass clippings, leaves, and other yard wastes, wastes from agricultural operations such as straw, stalks and leaves; wastes from the processing of agricultural products, such as gin trash, bagasse, grain hulls, peels, sorghum, sugar cane, animal byproducts, food industry sludge, paper industry sludge, clothing industry wastes or consumer wastes such as discarded clothing and furniture.

Generally speaking, the particles will be of relatively small size. For example, it is expected that utilizing particles which have a maximum size in the range of 1 mm to about 20 mm for a major portion, on a weight basis, of the particles in the aggregates will provide a good result. To provide the particles with this size, it is generally necessary to grind up the starting material. Generally, the paper or other material to be utilized is ground to a screen size of 10 cm or less, usually, to a screen size of 3 cm or less, and preferably to a screen size of between about 0.2 and about 2 cm. Hammer mills can be used.

By aggregate is meant a cluster of cellulose-containing particles. Generally speaking, the aggregates are formed from consolidated particles. Preferably, the aggregate is consolidated by compacting ground paper and/or vegetable matter particles under conditions of sufficient moisture, for example by pelletizing or briquetting, to form pellets or briquettes of cellulose-containing particles. For certain applications, however, the aggregate may be in the form of crumb or broken cake. For these applications, broken up pellets or briquettes form a highly suitable material.

The particle size and shape of the aggregates depends on the desired application. For application on the surface of the soil, a relatively small particle size is believed best suited. It should be sufficiently large, however, so that it is not displaced by wind. For deep burial, larger aggregates may be used. To form a ground cover, an intermediate size is probably best suited. Where the aggregates are to be tilled into the soil, a wide range of sizes are suitable, although small particles will be assimilated more quickly than larger ones, and will therefore provide quicker remediation as well as quicker release of nutrients and/or added materials.

Generally speaking, the particle size, as expressed in terms of average volume of a major portion of the aggregates, can range from about 0.01 cc to about 1200 cc. Usually, the aggregates will have a volume in the range of from about 0.1 cc to about 800 cc. Preferably, the aggregates will have a volume in the range of from about 0.5 cc to about 150 cc, because it is believed that aggregates having a volume in this range will be useful for most applications. However, for some applications, it may be desirable to form mixtures of aggregates with a volume in the range of 0.5 cc to 150 cc with smaller aggregates which may be in crushed or crumbled form such as those having a size in the range of from about 0.02 cc to about 0.5 cc., although even smaller aggregates such as those having a volume as small as 0.005 cc may also be used.

The aggregates can also be described as having a major dimension and a minor dimension. The minor dimension is preferably less than 5 cm to aid in breakdown and assimilation by the soil. The major dimension is preferably less than about 30 cm to aid in mixing in the soil with standard agricultural implements. The minor dimension is preferably greater than about 0.15 cm and the major dimension is preferably greater than about 0.3 cm for reasons of economy in production and handling. Generally speaking, the aggregates are produced in pellet or briquette form, and can have any desired configuration, such as circular, square, or flattened cross section. The currently preferred aggregate is presently an elongated extrudate with a circular cross-section, because it has been tested with good results. The presently preferred aggregate is generally arcuately shaped and has a length in the range of about 0.1 to about 30 cm and a diameter in the range of from about 0.1 to about 5 cm. Even more preferably, the extrudate has a length in the range of from about 1 to about 15 cm and a diameter in the range of from about 0.2 to about 1.0 cm. An extrudate having a length closely encompassed by the range of from about 2 to about 5 cm and a diameter in the range of from about 0.3 to about 0.8 cm has been tested in several related applications with good results. For fire ant control, it is preferred, however, that the maximum dimension be in the range of about 0.1 cm to about 1.0 cm.

The aggregates will generally have an apparent bulk density in the range of from about 140 kg/m$^3$ to about 550 kg/m$^3$ at a moisture level of about 20% by weight.

The formation of pellets of ground paper is known, but not commonly used in the paper recycling industry. A pelletizing machine which extrudes pellets in the form of an extrudate has been used with good results. It is also believed that a briquetting machine, such as is used for the manufacture of charcoal briquettes, would also be useful, as well as equipment for pelletizing animal feeds To form the aggregates, the selected cellulose-containing material or mixture thereof is first ground to a particle size suitable for pellet or briquette formation. Generally, the material is ground to a screen size of 10 cm or less, usually, to a screen size of 3 cm or less, and preferably to a screen size of between about 0.2 and about 2 cm. Hammer mills can be used. The aggregates thus contains discrete particles of the selected material(s) in comminuted form. The material is then pelletized or briquetted. If necessary, moisture is added in an amount sufficient to facilitate the completion of pellet or briquette formation. Small sized aggregates can be formed, if desired, by crumbling the resulting pellets or briquettes. The aqueous medium may contain a binding agent to facilitate pelletizing. Binding agents include paper products, clay, or starch based adhesives, for example. Preferably, the binding agent comprises paper prepared as hereinabove described.

The aqueous medium can be selected from a wide range of sources. Water is suitable. Other aqueous mediums containing organic matter are also suitable. Sewer sludge, paper pulp sludge, sludge containing animal wastes such as chicken litter and/or cattle manure, and slaughterhouse wastes are all suitable. If desired, a growth promoter such as a source of assimilable nitrogen, for example, which is sufficient to provide the aggregate product with a ratio of nitrogen to biodegradable carbon in the range of from about 1:20 to about 1:60 or even 1:90, on an atomic (elemental weight) basis can be incorporated into the product during the pelletizing process. However, for remediation uses, it is preferred that the aggregate not contain added assimilable nitrogen.

For remediation purposes, the aggregates can be applied to the soil in any desired manner. Generally, the aggregates will be broadcast on the soil surface. Generally speaking, for quickest assimilation, and thus remediation, it is desirable to mix the aggregates with the soil. This can be accomplished by conventional tilling after the aggregates have been broadcast on the soil surface, but usually to a depth of no greater than 61 cm. Most often, the aggregates will be tilled into the soil to a depth of no greater than about 15 cm because this can be accomplished using standard farm implements. Application is in an amount sufficient to provide a C:N atomic ratio between nitrogen from the source of animal waste and carbon from the cellulose of between about 10:1 to about 60:1, preferably in an amount to provide a C:N atomic ratio between nitrogen from the animal wastes and carbon from the cellulose of between about 20:1 to about 60:1, most preferably about 30:1. If desired, other growth promoters such as micronutrient combinations can be incorporated into the aggregates as well.

The amount of aggregates to be used can be determined by analysis of the land to be remediated or can be estimated from the amount of animal waste which has been deposited on the land. Generally speaking, the aggregates are applied in an amount of from about 0.2 to about 5 parts by weight for each part of waste on the area to be remediated, usually in an amount of from about 0.5 to about 2 parts for each part by weight of waste. If desired, the aggregates can be applied to the land together with the animal wastes, thereby avoiding the need to subsequently remediate. This can be accomplished by incorporating the animal wastes into the aggregates during the manufacturing process, or by mixing the aggregates with the animal wastes to form a mixture of animal wastes and aggregates and applying the mixture to the land, either in the form of a flowable slurry or in the form of spreadable solids using conventional spreading equipment.

One of the advantages of this embodiment of the invention is that it permits larger amounts of animal wastes to be spread over a given land area without causing pollution.

Where the aggregates are formed from recycled paper, they contain about 56% carbon with a carbon to nitrogen ratio of 500 to 1 and an aluminum content of 0.5%. Amending the soil at land application sites with the paper pellet will increase the carbon content in the soil, promote microbial growth and has the potential to utilize soil nitrogen and to precipitate phosphorus. If the pellet is applied at a rate of 1 lb/sq ft, the microbial degradation of the paper will theoretically consume N at a rate of 813 lb/acre and the aluminum has the potential to precipitate phosphorus at a rate of 653 lb/acre.

In another embodiment of the invention, is provided a method for controlling termite infestation employing the aggregates as described above. In accordance with the method, an area to be protected from the termite infestation is selected and aggregates of cellulose-containing particles containing at least one anti-termite agent are applied around the area to be protected.

The duration of an anti-termite agent effectiveness is greatly increased over current methods due to its being incorporated into the aggregates and being released over the decomposition period of the product. In essence, this method of applying a termiticide permits it to become a slow release, long acting product. The method is also safer for workers since it eliminates the handling and potential breathing of liquids and sprays of concentrated dangerous chemicals during application.

Normally, the area to be protected will contain a building. However, in certain parts of the country, such as New Orleans, termite damage to trees is a major problem, and it is within the scope of the invention to protect trees. Preferably, the area to be protected is surrounded with the aggregates. In the case of buildings, it is contemplated that the aggregates will be placed near the foundation. In the case of trees, it is contemplated that the aggregates will be positioned near the base of the tree. Generally speaking, the ground around the area to be protected will be covered with the aggregates. If desired, the aggregates can be buried in the ground around the area to be protected, such as by trenching or tilling techniques.

The aggregates containing the anti-termite agent are expected to function as a termite "bait"—where the termites are attracted to the product as a feed where they pick up the toxin and return to the colony to wipe it out, or as a "repellent"—where the termites either are repelled by a barrier of product or pick up toxins by contracting the product and are killed. The product is expected to be highly effective when applied as a landscape mulch in flowers beds surrounding residences and other structures to be protected, such as on an annual basis. The product is expected to be highly protective when buried in the soil, forming a barrier or bait to eradicate and/or repel subterranean termites. For use as a bait, it is preferred that the aggregates contain wood products.

The anti-termite agent is incorporated into the products by spraying liquid types onto the aggregates and mixing granular types with the aggregates. Generally speaking, the aggregates will contain less than 10% by weight of the anti-termite agent, usually less than 1% but greater than 0.06%. Anti-termite agents generally include toxins and repellents. The toxin can be of the bait type. Anti-termite agents (primarily repellents) which can be incorporated into the product and an exemplary wt % amount to incorporate into the aggregates include FMC Biflex TC (Bifenthrin-0.06%), FMC Talstar F (Bifenthrin-0.06%), DowElanco Dursban TC (Chlorpyrifos—0.5 to 2.0%), Whitmire Duraguard (Chlorpyrifos 1–2%), Whitmire Optem TC (Cyfluthrin 0.05–0.25% ), Zeneca Demon TC (Cypermethrin 0.25%), FMC Prevail FT (Cypermethrin 0.25–1.0% ), Agrevo 25 SC (Deltamethrin 0.075–0.125% ), Agrevo Tribute II (Fenvalerate 0.5–1.0%), Bayer Premise 2 (Imidacloprid 0.1%), FMC F3697 (Imidacloprid 0.01–0.1%), Zeneca Karate (Lambda-cyhalothrin 0.25%), Zeneca Commodore (Lambda-cyhalothrin 0.25%), Zeneca Prelude (Torpedo) (Perethrin 0.05–1.0%), and FMC Dragnet FT (Perethrin 0.3%). Boric acid can also be used if desired. Anti termite agents (primarily "baits") which can be incorporated into the product and an exemplary wt % amount to incorporate into the aggregates include DowElanco Sentricon (Hexaflumuron 0.5%), Am Cyanamid Co. Subterfuge (Hydramethylnon 0.3%), and FMC FirstLine GT (Sulfuramid 0.01%).

In another embodiment of the invention, the aggregates of cellulose particles as described above can be employed in a method for controlling fire ants. The method is carried out by selecting an area in which fire ant control is desired and applying aggregates of cellulose-containing particles containing a fire ant toxin to the area. Generally speaking, the area to be treated will be either a fire ant mount or a horticultural area. For fire ant mounds, generally from about 1 cc to about 500 cc of the aggregates will be applied, depending on the effectiveness of the toxin carried by the aggregates. For horticultural areas, the aggregates will either be dispersed around the area to be protected, similar to that described above for termite control, or, more preferably, mixed with the soil. For example, fire ants can be prevented from nesting in potted plants or planters by mixing an effective amount of the aggregates contained in the pot or planter, or by utilizing the aggregates containing the toxin as a cover mulch for the pot or planter. The same techniques can be applied to gardens or larger agricultural areas. For lawns, the aggregates can simply be broadcast on the surface.

The toxin can be added to the aggregates in the same manner as the anti-termite agents as described above. Suitable toxins are well known in the art. Examples include Ciba Logic (Fenoxycarb), Ciba Award (Fenoxycarb), Am. Cyanamid Co. Amdro (Hydramethylnon), Ciba Diazinon granules (Diazinon), Whitmire Ascend (Abermectin), US Borax (Boric Acid), Zeneca Fireban (Tefluthrin), and FMC Talstar (Bifenthrin). The amounts of toxin are similar to that described above for the termite application.

In another embodiment of the invention, the aggregates of cellulose particles as described above can be employed in a method for controlling plant growth. The method is carried out by selecting an area in which plant growth control is desired and applying aggregates of cellulose-containing particles containing a plant growth inhibitor to the area. Generally, the type of plant growth desired to be inhibited will be weed growth or grass growth. The area to be treated will generally comprise a horticultural area. In such case, the plant growth inhibitor will generally comprise an herbicide.

It is believed that best results will be achieved in this embodiment of the invention where the horticultural area contains growing plants of the desired variety. The aggregates are applied around the growing plants so as to achieve coverage of the ground. Generally speaking, the area around the growing plants where plant growth inhibition is desired will be covered to a depth of from about 0.5 inches to about 5 inches, usually from about 1 to about 3 inches. The method is believed particularly well suited for application to potted plants, planters, beds and garden areas. The plant growth toxin can be added to the aggregates during the manufacturing process as hereinabove described. For such uses, it is preferred that the aggregates contain plant nutrients, and, for paper-based products, a complexing agent to slow the release of aluminum.

In this embodiment of the invention, the duration of the herbicide's effectiveness is greatly increased over current methods due to its being incorporated into the aggregate and being released over the decomposition period of the aggregate. In essence, this method of applying the herbicide allows it to become a slow release herbicide. The method of incorporation and application uses less herbicides than the standard methods because none, or very little, is lost during the application to the target area. Currently 40% or more of the herbicides never effectively reach their target area due to wind, rain and water runoff. The ability of a given amount of herbicide to prevent and/or eradicate weeds is therefore increased. The method for application is also safer for workers since it eliminates the handling and potential breathing of liquids and sprays of concentrated dangerous chemicals during application. The method also eliminates the necessity of prolonged waiting periods (8 or more hours) before safe entry in enclosed buildings which have recently been treated with herbicides. The training required for safe herbicide use in accordance with the invention is also lower than that currently required.

Suitable plant toxins are well known and are generally termed herbicides. They are usually incorporated into the aggregates in an amount which constitutes less than about 10 wt % of the applied material. Examples include Surflan AS (Oryzalin), Gallery 75DF (Isoxaben), Snaphot 2G (Trifluralin), Factor (Prodamine), OH-2 (Oxyflurofen+Pendimethalin), Ronstar 50 WP (Oxadiazon), Ronstar G (Oxadiazon), Ornamental weed Grass (Pendimethalin), XL 2G (Benefrin+Oryzalin), O-O (Oxyfurofen+Oxidanzon), Rout (Oxyfurofen+Oxdiazon), Pennant 85.1 (Metolachlor).

While certain preferred embodiments of the invention have been described herein, the invention is not to be construed as so limited, except to the extent that such limitations are found in the claims.

We claim:

1. A method for reducing the potential for contaminated runoffs caused by excess application of animal wastes on agricultural lands, said method comprising:

collecting animal wastes selected from the group consisting of poultry litter and manure from poultry, swine, horses, dairy or cattle operations;

applying the collected animal wastes to agricultural land in an amount having a potential to contaminate surface water runoffs with high levels of nitrogen and phosphorus, and then applying to the agricultural land a sufficient quantity of a material selected from the group consisting of pellets, briquettes, broken cake and crumb comprising aggregates of ground paper to consume nitrogen and precipitate phosphorus thereby to reduce such potential;

wherein the aggregates are applied to the land in an amount of from about 0.2 to about 5 parts by weight of aggregates for each part by weight of animal wastes, wherein the aggregates have a major dimension in the range of 0.3 cm to 30 cm; and wherein a major portion, on a weight basis, of the aggregates have a volume in the range of 0.1 cc to 800 cc.

2. A method as in claim 1 further comprising tilling the aggregates into the soil.

3. A method as in claim 1 wherein the aggregates of ground paper contain a ratio of nitrogen to carbon of less than about 90:1 on an elemental weight basis.

4. A method as in claim 1 wherein the aggregates are applied in an amount in the range of from about 10 to about 60 parts by weight of aggregates, based on the weight of carbon on an elemental basis contained in the aggregates, for each part by weight of the animal wastes, based on the weight of nitrogen on an elemental basis, contained in the animal wastes.

5. A method as in claim 1 wherein a major portion, on a weight basis, of the aggregates have a volume in the range of 0.5 cc to 150 cc.

6. A method as in claim 1 wherein the aggregates have an apparent bulk density in the range of from about 140 $kg/m^3$ to about 550 $kg/m^3$.

* * * * *